(12) United States Patent
Fallon et al.

(10) Patent No.: US 6,888,035 B2
(45) Date of Patent: May 3, 2005

(54) HYDROGENATION OF CLEAVAGE EFFLUENTS IN PHENOL PRODUCTION

(75) Inventors: Kevin J. Fallon, Boston, MA (US); Chung-Ming Chi, Weymouth, MA (US); Henry Y. Hwang, Newton, MA (US); Frank A. Demers, Holderness, NH (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/363,571

(22) PCT Filed: Sep. 25, 2001

(86) PCT No.: PCT/US01/29938

§ 371 (c)(1),
(2), (4) Date: Feb. 28, 2003

(87) PCT Pub. No.: WO02/26680

PCT Pub. Date: Apr. 4, 2002

(65) Prior Publication Data

US 2004/0034256 A1 Feb. 19, 2004

Related U.S. Application Data

(60) Provisional application No. 60/235,127, filed on Sep. 25, 2000.

(51) Int. Cl.$^7$ .............................................. C07C 37/08
(52) U.S. Cl. ...................................................... 568/798
(58) Field of Search ........................................ 568/798

(56) References Cited

U.S. PATENT DOCUMENTS

| 3,436,429 A | | 4/1969 | Flickinger et al. ........... 260/621 |
| 5,015,786 A | * | 5/1991 | Araki et al. ................. 568/798 |
| 5,017,729 A | | 5/1991 | Fukuhara et al. ............ 568/798 |
| 5,160,497 A | * | 11/1992 | Juguin et al. ................ 568/798 |
| 5,245,090 A | * | 9/1993 | DeCaria et al. .............. 568/798 |
| 2003/0153793 A1 | * | 8/2003 | Sakuth et al. ................ 568/798 |

FOREIGN PATENT DOCUMENTS

GB    1207133 A  *  9/1970

* cited by examiner

*Primary Examiner*—Michael L. Shippen
(74) *Attorney, Agent, or Firm*—Darryl M. Tyus; Linda A. Kubena

(57) ABSTRACT

A method for producing phenol is disclosed which includes oxidizing cumene to form cumene hydroperoxide and acid cleavage to form cumene, phenol, acetone, and various byproducts, including alpha methylstyrene, followed by a subsequent hydrogenation of at least a part of the acetone and substantially all of the alpha methylstyrene.

21 Claims, 1 Drawing Sheet

HYDROGENATION OF CLEAVAGE EFFLUENTS IN PHENOL PRODUCTION

This application is a 371 of PCT/US01/29938 Sep. 25, 2001 which claims benefit of 60/235,127 Sep. 25, 2000.

The present invention relates generally to improvements in the production of phenol whereby coproduced acetone is substantially immediately hydrogenated into recyclable isopropanol byproduct, and alpha methylstyrene byproduct is substantially simultaneously hydrogenated into cumene for recycle. In addition, the methods of this invention reduce the formation of undesirable byproducts which would otherwise reduce product yields and more importantly increase the difficulty of phenol purification thereby realizing further process efficiencies.

BACKGROUND OF THE INVENTION

Most of the phenol used in the United States and elsewhere is made by the oxidation of cumene to form cumene hydroperoxide, followed by decomposition or cleavage of the cumene hydroperoxide to produce phenol and yielding acetone as a major coproduct. The first step in the reactor yields cumene hydroperoxide, which decomposes with dilute sulfuric acid or sulfur dioxide to the primary products, plus acetophenone and dimethyl phenyl carbinol. Other processes include sulfonation, chlorination of benzene and oxidation of benzene. The compound is purified by rectification.

Major uses of phenol include production of phenolic resins and para, para-bisphenol A; as a selective solvent for refining lubricating oils; in the manufacture of cyclohexanone, salicylic acid, phenolphthalein, pentachlorophenol, acetophenetidine, picric acid, germicidal paints, and pharmaceuticals; as well as use as a laboratory reagent. Special uses include dyes and indicators, and slimicides.

The conventional phenol process, which dates back to patents to Allied Chemical and Hercules Chemical Co. in the 1950s, is economical as long as there is adequate demand for the acetone coproduct. Because the end uses and rate of growth for phenol and acetone differ, however, with phenol generally experiencing higher growth rates, there has long been a desire to produce phenol without acetone.

In addition, the oxidation of cumene to cumene hydroperoxide (CHP) also results in the formation of some level of dimethylphenyl carbinol (DMPC) also known as dimethylbenzyl alcohol (DMBA). DMPC subsequently dehydrates in the cleavage system to form alpha methylstyrene (AMS) as a significant process byproduct. The AMS then has a known tendency to react with the phenol in the cleavage system to produce cumyl phenol or to dimerize into AMS dimers, both of which are heavier, undesired byproducts, and lead to overall yield loss. Moreover, if an acetone-containing stream is recirculated to an upstream stage, e.g., the cleavage system, the acetone has shown a tendency to form impurities originating from the acetone such as mesityl oxide or hydroxyacetone.

Another problem with the conventional processes for preparing phenol is that the conventional cleavage of cumene hydroperoxide is highly exothermic and requires heat removal to control exotherms, particularly because CHP at higher temperatures can undergo a dangerous thermal decomposition. In conventional processes, cooling can be accomplished by several methods. In one type of cooling scheme the effluent, containing approximately stoichiometric levels of acetone and phenol, as well as lesser amounts of AMS, is cooled and recirculated at the high recirculation ratios (between 20–50:1) that are necessary to control the exotherm. This results, however, in high levels of both AMS and acetone being present under highly reactive conditions, leading to high levels of residues, as well as impurities formed from acetone reactions such as aldol condensations.

Several prior art patents have endeavored to address one or more of the drawbacks, problems, or limitations of conventional phenol processes. U.S. Pat. No. 5,245,090 (DeCaria '090), which is incorporated herein by reference, teaches a two-stage process for producing phenol comprising the steps of decomposing cumene hydroperoxide in a first stage, and subjecting the product of the first stage to hydrogenation in a second stage to convert AMS in the first stage effluent stream to cumene, which is then recycled. The DeCaria '090 patent notes (col. 3, lines 25–32) that the first stage effluent stream must be allowed "sufficient contact time in the second reactor to effect essentially complete decomposition of the residual CHP to phenol and acetone and over 95% disappearance of the DMBA (same as DMPC) and DiCup and to effect virtually complete hydrogenation of AMS . . . to cumene." Subsequently, DeCaria '090 observes (col. 3, lines 32–26) that this "process can be run . . . with or without the recycle of a portion of the acetone product . . . ." Clearly, therefore, the DeCaria '090 patent does not contemplate the hydrogenation of acetone in the hydrogenation stage. This conclusion is reaffirmed by later portions of the DeCaria '090 patent (e.g., col. 6, lines 12–14). Indeed, claim 1 of DeCaria '090 is specifically directed to a method of making phenol and acetone. Thus, DeCaria '090 does not address the problem of how to transform the acetone coproduct of phenol production into a more useful product or recycle stream or how to reduce formation of undesirable byproducts. Furthermore, a problem with the DeCaria '090 process scheme is the probable poor selectivity of the hydrogenation in the presence of carbonyl compounds. The carbonyl bond in the acetone byproduct can be hydrogenated to form isopropanol. Judged strictly as a byproduct, however, isopropanol is of lesser value than acetone. In fact an appreciable though declining percentage of the acetone in the world is produced from isopropanol as a feedstock.

U.S. Pat. No. 5,015,786 (Araki '786), which is incorporated herein by reference, teaches a process for preparing phenol by the cumene process including the step of converting acetone coproduced with the phenol into isopropanol, thereafter alkylating benzene with the isopropanol and, optionally, with propylene, using a zeolite catalyst to produce cumene, thereby forming phenol without the usual acetone coproduct. Araki '786, however, fails to address the problem of how to handle the AMS component and the other byproduct components of the effluent from the CHP cleavage/decomposition stage.

Somewhat similar to Araki '786 is U.S. Pat. No. 5,017,729 (Fukuhara '729), which is also incorporated herein by reference. Fukuhara '729 teaches a multi-step phenol production process comprising: (a) reacting benzene with propylene to synthesize cumene, (b) oxidizing the cumene of step (a) into cumene hydroperoxide, (c) acid cleaving cumene hydroperoxide into phenol and acetone, (d) hydrogenating the acetone of step (c) into isopropanol, (e) dehydrating the isopropanol of step (d) into propylene, and (f) recycling the propylene of step (e) to step (a). It is also possible to take a propylene product from step (e). The acetone byproduct produced upon preparation of phenol is converted into propylene which Fukuhara '729 teaches is useful by itself for any other uses or which may be recycled to the phenol-producing process. Fukuhara '729 is also similar to the Araki '786 patent in failing to address the problems of handling the AMS and other byproduct components of the effluent from the CHP cleavage/decomposition step.

U.S. Pat. No. 5,160,497 (Juguin '497), which is also incorporated herein by reference, teaches still another variation on a phenol production process addressed specifically to dealing with the less-desired acetone coproduct. Thus, the Juguin '497 patent observes (col. 1, lines 58–61) that: "Nowadays, the main handicap of this [cumene-to-phenol] process lies in the obligatory coproduction of 0.61 ton of acetone per ton of phenol, because the demand for phenol increases much more rapidly than that for acetone." The improvement of the Juguin '497 patent is stated to be (col. 1, line 66—col. 2, line 2) "in partly or totally hydrogenising the acetone produced into isopropyl alcohol, and in recycling at least partly the latter to the stage of alkylation of benzene where, after dehydration into propene, it will be converted again into cumene."

The Juguin '497 patent further notes, however, that successful practice of this invention is highly catalyst dependent because (col. 2, lines 8–12) the conventional alkylation catalysts "are not adapted to the reaction of alkylation of benzene in the presence of isopropyl alcohol because they are very sensitive to water . . . ." Instead of using conventional aluminum chloride or phosphoric acid catalysts, Juguin '497 turns to a specific class of zeolite catalyst which had been found to be stable in the presence of the steam generated by dehydration of isopropyl alcohol.

The overall method taught by the Juguin '497 patent is a multi-step process comprising in sequence: an alkylation stage (carried out with at least one catalyst based on a dealuminized Y zeolite having a particular $SiO_2/Al_2O_3$ molar ratio) to form an effluent stream containing cumene, unreacted benzene, and polyisopropylbenzene; a fractionation step to separate a cumene fraction and a polyisopropylbenzene fraction; a transalkylation stage (again carried out using the particular dealuminized Y zeolite catalyst) where polyisopropylbenzene and benzene are reacted to form additional cumene; a further fractionation step to recover the additional cumene from transalkylation; an oxidation step to oxidize cumene into cumene hydroperoxide; a cleavage step to cleave the cumene hydroperoxide into phenol and acetone; another fractionation step to separate phenol and acetone; and, finally, the step of hydrogenating the acetone into isopropyl alcohol in the presence of a nickel-on-silica catalyst, and recycling the isopropyl alcohol as a feed to the alkylation stage. The Juguin '497 patent does not address how to handle AMS and other byproducts in the effluent from the CHP cleavage stage or how to minimize formation of residue products.

As a result, there remains an unmet need in this art for an integrated cumene-based phenol production method that reduces the formation of undesirable byproducts from AMS and acetone. The aforementioned drawbacks and limitation of the prior art are overcome, in whole or in part, with the methods of this invention for an integrated, efficient, low-residue phenol process which includes hydrogenation of cleavage effluents.

OBJECTS OF THE INVENTION

Accordingly, a principal object of this invention is to provide improved methods, which include a hydrogenation step, for the production of phenol from cumene.

It is a general object of this invention to provide an integrated cumene-to-phenol method in which the principal undesirable coproducts and/or byproducts from the cleavage system are converted by hydrogenation into products which can be recycled as feeds to one or more upstream process steps before they can further react to form other heavier residues.

A specific object of this invention is to substantially simultaneously hydrogenate, utilizing a suitable hydrogenation catalyst: (a) substantially all of the acetone coproduct in the effluent from the cleavage system of a phenol process to isopropyl alcohol; and (b) substantially all of the alpha methylstyrene byproduct in the cleavage system effluent to cumene.

Other objects and advantages of the present invention will in part be obvious and will in part appear hereinafter. The invention accordingly comprises, but is not limited to, the methods and related apparatus, involving the several steps and the various components, and the relation and order of one or more such steps and components with respect to teach of the others, as exemplified by the following description and the accompanying drawing. Various modifications of and variations on the method and apparatus as herein described will be apparent to those skilled in the art, and all such modifications and variations are considered within the scope of the invention.

SUMMARY OF THE INVENTION

In this invention, acetone and alpha methylstyrene in the effluent from the cleavage system of a cumene-based phenol process are both hydrogenated substantially simultaneously immediately downstream of the cleavage system. It is thereby possible to recover isopropanol by distillation downstream of the hydrogenation step and recycle it back to a benzene alkylation step in place of propylene to produce cumene. The hydrogenation system of this invention can be integrated with the cleavage system in such a way as to improve overall yield and product purity. Early hydrogenation of alpha methylstyrene, directly downstream of the cleavage system, eliminates the active styrenic functionality from forming heavies such as dimers and cumylphenols. Of comparable importance, elimination of the acetone can reduce the ability of the components in the effluent from the cleavage system to form close boiling impurities that are difficult to separate from phenol, such as hydroxyacetone, mesityl oxide and methylbenzofuran. Selection of appropriate hydrogenation catalyst facilitates carrying out the immediate, substantially simultaneous hydrogenation of acetone and AMS in the effluent from the cleavage system.

DETAILED DESCRIPTION OF PREFERRED EMBODIMENTS

Figure 1:
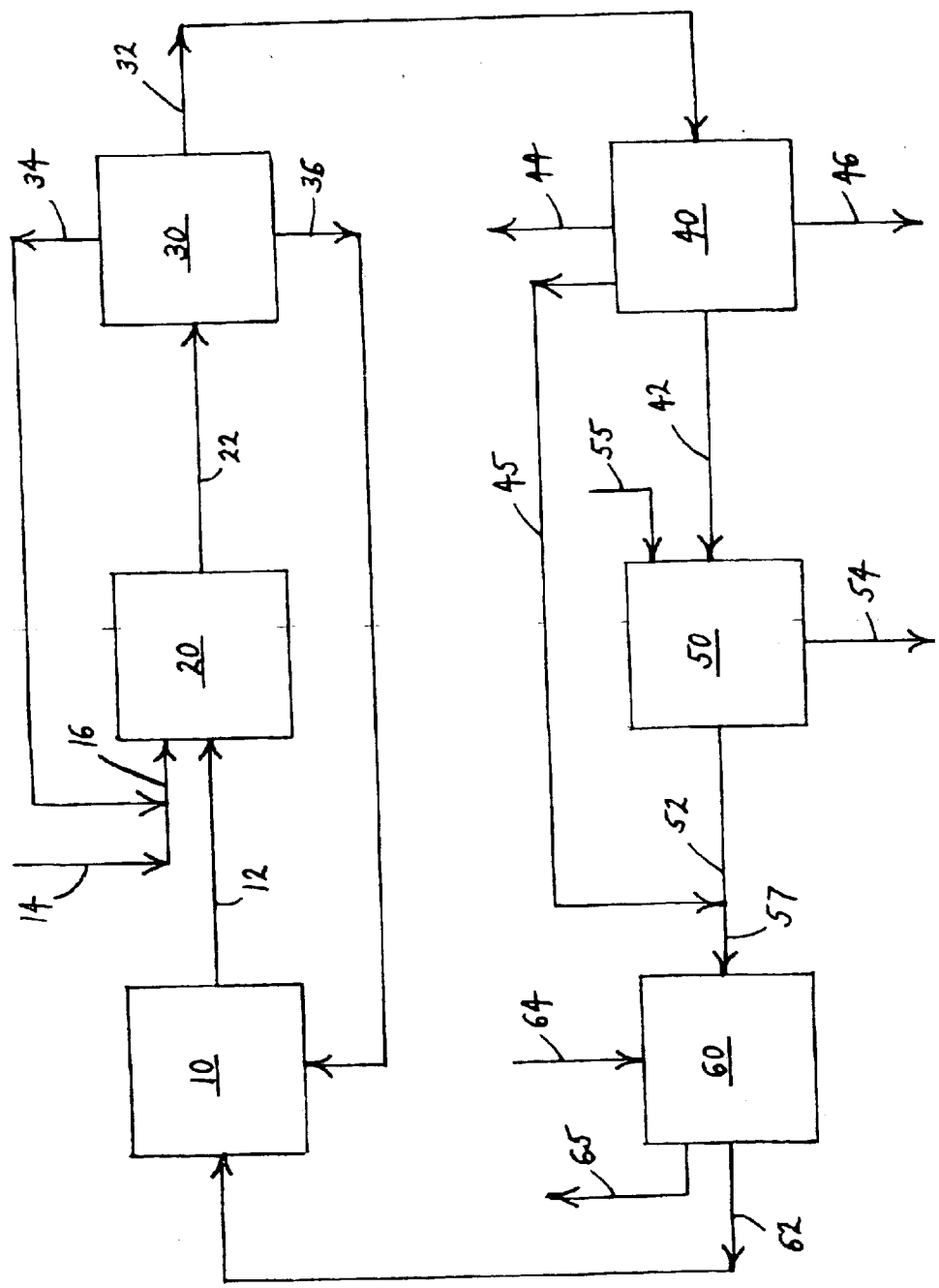
FIG. 1 is a process flow diagram schematically illustrating an embodiment of a phenol production process incorporating hydrogenation of cleavage effluents and recycle of converted products according to the present invention.

The methods of this invention can best be understood by reference for FIG. 1. As seen in FIG. 1, a stream (such as stream 62) as produced by conventional cumene oxidation technologies, and containing primarily cumene and cumene hydroperoxide, together with lesser amounts of dimethylphenyl carbinol, acetophenone, and other minor components, is fed to the cleavage reactor system 10. In the cleavage reactor system 10, cumene hydroperoxide undergoes an acid-catalyzed decomposition reaction to phenol and acetone. The acid catalyst in reactor 10 may include homogenous acids such as sulfuric acid, sulfur dioxide, hydrochloric acid, nitric acid, or phosphoric acid, or may include heterogeneous acidic catalysts such as zeolite beta, acidic zeolite-based catalysts, such as MCM-22, MCM-36, MCM-49, MCM-56, ERB-1, ITQ-1, ITQ-2, ITQ-3, SSZ-25, PSH3 and the like, ultrastable zeolite Y, ZSM-5, mordenite, metal oxides, alumina or clays. Usually a small quantity of water is also present in this stream to achieve the desired reaction chemistry. In addition to the decomposition reaction of cumene hydroperoxide, the acidic conditions of the cleavage reactor system 10 promote the dehydration of the dimethylphenyl carbinol byproduct to form alpha methylstyrene.

The cleavage system 10 is a highly exothermic reaction which generates heat that may be removed from the effluent stream 12 coming from reactor 10 by any number of means known to those skilled in the art. These can include but at not limited to tubular reactors, pump-around cooling, vaporization of the more volatile components, condensation and reflux of the vaporized components, or recycle of liquid light end components from the downstream process, for example by recycle stream 36 from separation step 30.

The acid cleavage reactor effluent 12 contains cumene, phenol, acetone, alpha methylstyrene, water, acetophenone, and other minor impurities. Stream 12 enters the hydrogenation reactor system 20, where the alpha methylstyrene is hydrogenated either partially or substantially completely to cumene, and, substantially simultaneously, the acetone is converted either partially or substantially completely to isopropanol. Fresh hydrogen stream 14 together with recycle hydrogen stream 34 from separation system 30 are fed to hydrogenation reactor system 20 to provide an excess of hydrogen in the hydrogenation stage. The excess unreacted hydrogen is disengaged at separation stage 30 and, preferably, recycled to hydrogenation stage 20 via recycle stream 34.

A portion of the isopropanol and/or acetone from stage 30, as well as possibly acetone 46 from stage 40, may be recycled as stream 36 to the cleavage reactor system 10 to facilitate heat removal. The product stream 32 from stage 30, comprising isopropanol and/or acetone, phenol, and cumene (both excess-cumene as well as cumene formed by hydrogenation of AMS), is sent to downstream distillation system 40. In distillation system 40, stream 32 is separated into the respective products phenol 44, acetone 46 (if applicable), isopropanol 42 and cumene 45 which is sent to oxidation stage 60. Depending on the acid catalyst employed, a neutralization step employing an alkaline material, either by direct injection of alkali or by anionic exchange, may also be required at this point in the process.

Isopropanol 42 is fed to a cumene process alkylation unit 50 for use as a benzene alkylating material. Fresh propylene 55 may be needed to supplement the isopropanol 42 as the C3 alkylating agent. Byproduct water 54 and cumene product 52 are produced. The cumene stream 52 from alkylation system 50 is mixed with cumene stream 45 from stage 40, and the combined stream 57 is sent to oxidation stage 60, where the cumene is reacted with oxygen in air feed stream 64 to form cumene hydroperoxide stream 62 for feeding to cleavage reactor 10. Stream 62 will typically include about 5–20% of unoxidized cumene plus various impurities and byproducts as discussed above.

The cleavage stage (reference numeral 10 in FIG. 1) according to the present invention may operate at temperatures of about 50° C. to 100° C. Cleavage catalysts suitable for the present invention include sulfuric acid; sulfur dioxide; hydrochloric acid; phosphoric acid, zeolite-type catalyst (e.g., beta; zeolite Y; ZSM-5); acidic zeolite-based catalysts (e.g., MCM-22, MCM-36, MCM-49 and MCM-56); mordenite; acidic clays; and alumina. Feed (stream 62) to cleavage stage 10 will typically comprise about 20–95% CHP, 5–20% cumene, and 2–10% DMPC.

The hydrogenation stage (reference numeral 20 in FIG. 1) according to the present invention may operate at temperatures of about 40° C. to 150° C. and at pressures about 50 to 500 psig. Ratios of hydrogen in stage 20 to the acetone and AMS in effluent stream 12 may range from above about 1 to about 30 molar, preferably 3 to 10 molar, thereby representing a molar excess of hydrogen. Suitable catalysts for the hydrogenation stage 20 of this invention include Group VIII elements, noble metals, nickel, copper, chromium and combinations and oxides thereof. Hydrogenation stage 20 may be noble metals operated so as to substantially fully or partially convert acetone in stream 12 to isopropyl alcohol.

The alkylation stage (reference numeral 50 in FIG. 1) may be operated with feeds of benzene and isopropanol or isopropanol/propylene mixtures at temperatures of about 80° C. to 200° C. in the liquid phase using zeolite-type catalysts (e.g., beta and Y) or acidic zeolite-based alkylation catalysts (e.g., MCM-22, MCM-36, MCM-49, and MCM-56, ITQ-1, ITQ-2, ITQ-3, SSZ-25 and PSH3).

The acidic zeolite-based alkylation catalysts have been found to have particular utility in the practice of this invention. The following U.S. patents and publications, each of which is incorporated herein by reference, teach the preparation and/or use of various acidic zeolite-based catalysts: U.S. Pat. No. 6,096,288 (Roth); U.S. Pat. No. 6,077,498 (Diaz Cabañas); WO097/19021 (Corma); U.S. Pat. No. 6,063,262 (Dhingra); U.S. Pat. No. 6,049,018 (Calabro); U.S. Pat. No. 5,437,855 (Valyocsik); U.S. Pat. No. 5,670,131 (Valyocsik); U.S. Pat. No. 5,362,697 (Fung); U.S. Pat. No. 5,346,685 (Moini); U.S. Pat. No. 5,236,575 (Bennett); U.S. Pat. No. 5,068,096 (Valyocsik); U.S. Pat. No. 5,104,495 (Chang); U.S. Pat. No. 4,981,663 (Rubin); U.S. Pat. No. 4,696,807 (Chu); U.S. Pat. No. 4,791,088 (Chu); U.S. Pat. No. 5,441,721 (Valyocsik); U.S. Pat. No. 4,954,325 (Rubin); U.S. Pat. No. 5,173,281 (Chang); U.S. Pat. No. 5,043,512 (Chu); U.S. Pat. No. 5,488,194 (Beck); and U.S. Pat. No. 4,439,409 (Puppe); U.S. Pat. No. 4,826,667 (Zones). Several of these patents teach the utility of acidic zeolite-based catalysts materials in alkylation and other hydrocarbon processes, although not specifically in connection with cumene-based phenol production.

The oxidation stage (reference numeral 60 in FIG. 1) may be operated with air and cumene feeds at temperatures of about 60° C. to 120° C. and pressures of about 0–100 psig, with cumene recycle to obtain reactor effluent (stream 62) CHP compositions from about 15–35 wt. % CHP. It is preferred to maintain a flowrate of air in air stream 64 to oxidation stage 60 so as to provide about 30% molar excess oxygen in stage 60 based on the flow of cumene in feed 57. Excess air is vented by vent stream 65.

The following example will further illustrate the methods of the present invention.

EXAMPLES

Examples 1A through 3C show the results of hydrogenation experiments obtained using a batch autoclave. In each example, 5 grams of catalyst and 150–180 grams of liquid hydrocarbon was charged to a 300 ml autoclave. The batch autoclave was equipped with a twin-impeller agitator operating at a speed of 600 RPM. Reactor pressure was maintained with a hydrogen cylinder of constant supply pressure. Samples were taken at various times throughout the experiment and analyzed via gas chromatography. The feed to the batch hydrogenation reactor in each example was chosen to be representative of that to a CHP cleavage reactor when operating with a portion of the feed derived by recycling some of the hydrogenation reactor effluent.

Example 1A

Operating condition: 5 g of Engelhard E-540, a Cu/Mn catalyst, and 150 g of reaction mixture at reaction temperature of 120C and hydrogen partial pressure of 210 psig.

Feed composition: 36.1 wt % of acetone, 1.1 wt % of isopropanol, 19.6 wt % of cumene 4.0 wt % of Alpha-methylstyrene, 0.3 wt % of dimethylphenylcarbinol (DMPC), and 38.8 wt % of phenol.

| | Reaction Time (hrs) | | | | |
|---|---|---|---|---|---|
| Conversion | 1 | 2 | 3 | 5 | 7.0 |
| Acetone to Isopropanol (IPA), % | 2.9 | 6.8 | 10.7 | 17.9 | 24.9 |
| Alpha-methylstyrene (AMS) to Cumene, % | 4.0 | 6.7 | 10.5 | 19.0 | 25.4 |

ND: not detected

Example 1B

Operating condition: 5 g of Engelhard E-540, a Cu/Mn catalyst, and 150 g of reaction mixture at reaction temperature of 154° C. and hydrogen partial pressure of 170 psig.

Feed composition: 15.7 wt % of acetone, 22.6 wt % of isopropanol, 21.7 wt % of cumene, 1.7 wt % of Alpha-methylstyrene, 0.3 wt % of dimethylphenylcarbinol (DMPC), and 37.9 wt % of phenol.

| | Reaction Time (hrs) | | |
|---|---|---|---|
| Conversion | 1 | 2 | 2.5 |
| Acetone to Isopropanol (IPA), % | 11.3 | 23.5 | 29.9 |
| Alpha-methylstyrene (AMS) to Cumene, % | 11.3 | 23.2 | 30.0 |

Example 2A

Operating condition: 5 g of copper chromite, ~42% CuO/~39% Cr$_2$O$_3$ purchased from Alfa Aesar, and 180 g of reaction mixture at reaction temperature of 120° C. and hydrogen partial pressure of 200 psig Feed composition: 39.3 wt % of acetone, 0.4 wt % of isopropanol, 18.8 wt % of cumene, 3.8 wt % of Alpha-methylstyrene, 0.3 wt % of dimethylphenylcarbinol (DMPC), and 37.4 wt % of phenol.

| | Reaction Time (hrs) | | |
|---|---|---|---|
| Conversion | 1 | 2.5 | 4.5 |
| Acetone to Isopropanol (IPA), % | 1 | 2.4 | 5.4 |
| Alpha-methylstyrene (AMS) to Cumene, % | 0 | <1 | 3.6 |

Example 2B

Operating condition: 5 g of copper chromite, ~42% CuO/~39% Cr$_2$O$_3$ purchased from Alfa Aesar, and 180 g of reaction mixture at reaction temperature of 150° C. and hydrogen partial pressure of 180 psig Feed composition: 30.0 wt % of acetone, 4.6 wt % of isopropanol, 19.9 wt % of cumene, 3.5 wt % of Alpha-methylstyrene, 0.3 wt % of dimethylphenylcarbinol (DMPC), and 41.4 wt % of phenol.

| | Reaction Time (hrs) | | |
|---|---|---|---|
| Conversion | 1 | 3 | 5 |
| Acetone to Isopropanol (IPA), % | 3.7 | 10.5 | 17.6 |
| Alpha-methylstyrene (AMS) to Cumene, % | 3.8 | 11.4 | 18.7 |

Example 3A

Operating condition: 5 g of Engelhard Na promoted Ni-5256, a Ni/Na catalyst, and 150 g of reaction mixture at reaction temperature of 81° C. and hydrogen partial pressure of 67 psig Feed composition: 27.6 wt % of acetone, 5.1 wt % of isopropanol, 17.2 wt % of cumene 3.8 wt % of Alpha-methylstyrene, 1.0 wt % of dimethylphenylcarbinol (DMPC), 2.0 wt % of cyclohexanone+cyclohexanol and 42.4 wt % of phenol.

| | Reaction Time (hrs) | | | |
|---|---|---|---|---|
| Conversion | 0.5 | 1 | 2 | 4 |
| Acetone to Isopropanol (IPA), % | <1 | <1 | 3.1 | 6.6 |
| Alpha-methylstyrene (AMS) to Cumene, % | 65.8 | 95.7 | 98.9 | 98.8 |

Example 3B

Operating condition: 5 g of Engelhard Na promoted Ni-5256, a Ni/Na catalyst, and 150 g of reaction mixture at reaction temperature of 71° C. and hydrogen partial pressure of 150 psig Feed composition: 24.4 wt % of acetone, 9.1 wt % of isopropanol, 18.2 wt % of cumene 4.1 wt % of Alpha-methylstyrene, 1.0 wt % of dimethylphenylcarbinol (DMPC), 2.5 wt % of cyclohexanone+cyclohexanol and 39.7 wt % of phenol.

| | Reaction Time (hrs) | | | |
|---|---|---|---|---|
| Conversion | 0.5 | 1 | 2 | 4 |
| Acetone to Isopropanol (IPA), % | <1 | 3.7 | 10.2 | 19.6 |
| Alpha-methylstyrene (AMS) to Cumene, % | 85.4 | 98.9 | 99.5 | 99.4 |

Example 3C

Operating condition: 5 g of Engelhard Na promoted Ni-5256, a Ni/Na catalyst, and 150 g of reaction mixture at reaction temperature of 77° C. and hydrogen partial pressure of 146 psig Feed composition: 34.6 wt % of acetone, 0.1 wt % of isopropanol, 16.5 wt % of cumene 2.5 wt % of Alpha-methylstyrene, 1.0 wt % of dimethylphenylcarbinol (DMPC), and 44.9 wt % of phenol.

| | Reaction Time (hrs) | | | |
|---|---|---|---|---|
| Conversion | 1 | 2 | 3 | 5 |
| Acetone to Isopropanol (IPA), % | 4.5 | 9.3 | 14.8 | 22.8 |
| Alpha-methylstyrene (AMS) to Cumene, % | 94.6 | 96.4 | 99.1 | 99.6 |

Example 4

A cumene hydroperoxide stream containing 80% CHP, 5% DMPC, and the balance primarily cumene is sent to a cleavage reactor containing zeolite beta. The reaction proceeds in the liquid phase at 85° C. and 7 bar (g) at a net feed weight hourly space velocity of 1.0. A recirculated hydrogenation effluent about 30 times the mass flow of the CHP feed is combined with the CHP at the same temperature. The recycle stream contains about 48 wt.% phenol, 30 wt.% isopropanol and 12 wt.% cumene.

The liquid effluent from the cleavage reactor is fed to a fixed bed hydrogenation reactor containing Rainey nickel catalyst, in the presence of hydrogen gas. The reaction is conducted at 120° C. and 22 bar, with excess hydrogen at a hydrogen to acetone and AMS molar ratio of 8:1. Excess hydrogen is disengaged from the effluent, and recycled back to the hydrogenation reactor. Acetone conversion to isopropanol and AMS conversion to cumene are in excess of 99%. The liquid effluent is partly recycled to the cleavage reactor as described above and partly sent to a separation stage.

The isopropanol recovered from the separation stage is fed to an alkylation unit using zeolite catalyst to produce cumene. The cumene produced in the alkylation unit is combined with cumene recovered from the separation stage and the mixed stream is sent to a cumene oxidation reactor to form CHP.

It will be apparent to those skilled in the art that other changes and modifications may be made in the above-described apparatus and methods for hydrogenation of cleavage effluents in phenol production without departing from the scope of the invention herein, and it is intended that all matter contained in the above description shall be interpreted in an illustrative and not a limiting sense.

We claim:

1. A method for producing phenol comprising the steps of:
   (a) oxidizing cumene to form cumene hydroperoxide;
   (b) reacting cumene hydroperoxide by acid cleavage to form an acid cleavage effluent stream which comprises cumene, phenol, acetone, and various byproducts including alpha methylstyrene;
   (c) separating a phenol product; and
   (d) hydrogenating the acid cleavage effluent stream immediately downstream from said reaction step (b) in a hydrogenation reaction carried out under hydrogenation conditions suitable for simultaneously hydrogenating at least a part of the acetone and at least a part of the alpha methylstyrene byproducts of said acid cleavage effluent stream wherein said hydrogenation step (d) is carried out in the presence of a suitable catalyst wherein said catalyst is selected from the group consisting of $Cu/Cr_2O_3$, Ni/Na, Cu/Mn, and Rainey nickel.

2. The method according to claim 1 wherein the hydrogenation step (d) includes hydrogenating substantially all of the alpha methylstyrene.

3. The method according to claim 1 or 2 wherein said hydrogenation conditions include providing a molar excess of hydrogen in the hydrogenation step (d).

4. The method according to claims 1 or 2 wherein said hydrogenation conditions include a temperature in the range of about 40° C. to 150° C., a pressure in the range of about 50 to 500 psig, and a molar ratio of hydrogen relative to the acetone and alpha methylstyrene content of said acid cleavage effluent stream of at least 1 to about 30.

5. The method according to claim 1 or 2 wherein the molar ratio of hydrogen relative to the acetone and alpha methylstyrene content of said acid cleavage effluent stream is in the range of 3–10.

6. The method according to claim 1 further comprising the steps of:
   (c) separating excess hydrogen from a hydrogenation effluent stream earning from the hydrogenation step (d) and
   (f) recycling that excess hydrogen back to the hydrogenation step (d).

7. The method according to claim 1 or 2 wherein at least a portion of the acetone in said acid cleavage effluent stream is hydrogenated to isopropanol and substantially all of the alpha methylstyrene is hydrogenated to cumene in said hydrogenation step (d).

8. The method according to claim 1 or 2 wherein substantially all of the acetone in said acid cleavage effluent stream is hydrogenated to isopropanol in said hydrogenation step (d).

9. The method according to claim 1 or 2 wherein at least a portion of a liquid phase of said hydrogenation effluent stream is recycled back to said reaction step (b).

10. The method according to claim 1 or 2 further comprising the steps of:
    (e) recovering isopropanol by distillation downstream of said hydrogenation step (b); and
    (f) feeding at least a portion of the recovered isopropanol to an alkylation reactor in combination with benzene and propylene as needed to produce the cumene for forming said cumene hydroperoxide in the cumene oxidizing step (a).

11. A method for producing phenol comprising the steps of:
   (a) oxidizing cumene to form cumene hydroperoxide;
   (b) reacting cumene hydroperoxide by acid cleavage to form an acid cleavage effluent stream which comprises cumene, phenol, acetone, and various byproducts including alpha methylstyrene;
   (c) separating a phenol product; and
   (d) hydrogenating the acid cleavage effluent stream immediately downstream from said reaction step (b) in a hydrogenation reaction carried out under hydrogenation conditions suitable for simultaneously hydrogenating at least a part of the acetone and at least a part of the alpha methylstyrene byproducts of said acid cleavage effluent stream
wherein at least a portion of a liquid phase of said hydrogenation effluent stream is recycled back to said reaction step (b).

12. The method according to claim 11 wherein the hydrogenation step (d) includes hydrogenating substantially all of the alpha methylstyrene.

13. The method according to claim 11 wherein said hydrogenation conditions include providing a molar excess of hydrogen in the hydrogenation step (d).

14. The method according to claim 11 wherein said hydrogenation conditions include a temperature in the range of about 40° C. to 150° C., a pressure in the range of about 50 to 500 psig, and a molar ratio of hydrogen relative to the acetone and alpha methylstyrene content of said acid cleavage effluent stream of at least 1 to about 30.

15. The method according to claim 11 wherein the molar ratio of hydrogen relative to the acetone and alpha methylstyrene content of said acid cleavage effluent stream is in the range of 3–10.

16. The method according to claim 11 wherein said hydrogenation step (d) is carried out in the presence of a suitable catalyst.

17. The method according to claim 16 wherein said catalyst is selected from the group consisting of Group VIII elements, noble metals, nickel, copper, chromium, and claim noble metals combinations and oxides thereof.

18. The method according to claim 17, wherein said catalyst is selected from the group consisting of $Cu/Cr_2O_3$, Ni/Na, Cu/Mn, and Rainey nickel.

19. The method according to claim 11 further comprising the steps of:

(e) separating excess hydrogen from a hydrogenation effluent stream coming from the hydrogenation step (d) and
   (f) recycling that excess hydrogen back to the hydrogenation step (d).

20. The method according to claim 11 wherein at least a portion of the acetone in said acid cleavage effluent stream is hydrogenated to isopropanol and substantially all of the alpha methylstyrene is hydrogenated to cumene in said hydrogenation step (d).

21. The method according to claim 11 wherein substantially all of the acetone in said acid cleavage effluent stream is hydrogenated to isopropanol in said hydrogenation step (d).

* * * * *